United States Patent

Cohen et al.

[11] Patent Number: 5,876,736
[45] Date of Patent: Mar. 2, 1999

[54] SKIN REVITALIZING MAKEUP

[75] Inventors: Kenneth A. Cohen, Germantown; Daniel Ross, Memphis; Harold Suss, Germantown, all of Tenn.

[73] Assignee: Maybelline Intermediate Company, Memphis, Tenn.

[21] Appl. No.: 729,994

[22] Filed: Oct. 11, 1996

Related U.S. Application Data

[63] Continuation of Ser. No. 360,076, Dec. 20, 1994, abandoned.

[51] Int. Cl.$^6$ ............................... A61R 7/00; A61R 7/48
[52] U.S. Cl. ................. 424/401; 424/195.1; 514/547; 514/937; 514/938
[58] Field of Search ............................ 424/70.1, 70.11, 424/78.03, 401, 195.1; 514/847, 937, 938

[56] References Cited

U.S. PATENT DOCUMENTS

| | | | |
|---|---|---|---|
| 4,105,783 | 8/1978 | Yu et al. ................................. | 424/283 |
| 4,543,250 | 9/1985 | Witt ........................................... | 424/70 |
| 5,244,665 | 9/1993 | Natraj et al. ............................ | 424/401 |
| 5,391,373 | 2/1995 | Mausner ................................. | 424/401 |
| 5,422,112 | 6/1995 | Williams ................................. | 424/401 |

FOREIGN PATENT DOCUMENTS 62268752  7/1989  Japan .

*Primary Examiner*—Sally Gardner-Lane
*Attorney, Agent, or Firm*—Sherman and Shalloway

[57] ABSTRACT

An emulsified cosmetic makeup for revitalizing, smoothing, moisturizing and tightening the skin is disclosed. The composition comprises cosmetically effective amounts of a film forming agent containing plant polysaccharides and hydrolyzed casein, at least one sunscreen agent, at least one natural exfoliating agent, at least one moisturizer/rehydrating agent encapsulated in liposome vessicles, at least one preservative, at least one antioxidant agent, at least one cosmetically acceptable pigment and at least one emulsifier.

10 Claims, No Drawings

SKIN REVITALIZING MAKEUP

This is a continuation of application Ser. No. 08/360,076 filed Dec. 20, 1994 which is now abandoned.

BACKGROUND OF THE INVENTION

1. Field of the Invention

The present invention relates to a makeup composition and method for treating skin, and more particularly, to an improved pigmented makeup cosmetic composition which, when applied topically to exposed human skin, provides effective protection from the sun, moisturizes and revitalizes the skin as well as provides an attractive pigment thereto.

2. Description of the Prior Art

Aging, environmental conditions, such as heating and air conditioning, exposure to the sun and environmental pollution exert negative effects on human skin and result in wrinkles, sagging, loss of elasticity and firmness, dryness, changes in complexion and other cosmetically undesirable effects. A number of skin cream compositions exist that contain ingredients to counteract some of the effects of stress on the skin.

Sunscreens provide protection from sun-induced skin damage that accelerates skin aging. A number of patents relate generally to anti-aging cosmetic compositions that include a broad range of ingredients including for example, free radical activity retarding compounds, titanium dioxide as sunscreen, antioxidants, emulsifiers, thickeners and colorants (U.S. Pat. No. 5,093,109) or plant and yeast extracts, vitamin E or C for elasticity, silicone for firmness and sunscreens (U.S. Pat. No. 5,204,105) or skin cream compositions containing serum protein complex with hydrolyzed animal protein, protein-amino-acid-vitamin-nucleotide complex, dimethylsilanoyl hyaluronate complex and small micellar complexes containing various ingredients, such as for example panthenol (U.S. Pat. No. 5,254,331). Many cosmetic compositions and skin protective compositions contain titanium dioxide, alone, mixed with or treated with a silicone compound (U.S. Pat. No. 4,801,445) or titanium dioxide coated with or mixed with mica and or silicone (U.S. Pat. No. 4,820,508) or microfine particles of titanium oxide (U.S. Pat. No. 5,032,390 and 5,250,289).

However, sunscreens and other anti-aging agents are not effective in revitalizing skin that has already been damaged by sun, aging or other factors. Cosmetic compositions that counteract the effects of natural aging on the skin do not retard the effects of sunlight and do not conceal damage that has already occurred to the skin due to the natural aging process. U.S. Pat. No. 4,839,161 to Bowser, et al. discloses a therapeutic composition for alleviating or preventing sun-induced desquamation, which includes as an active ingredient a $C_3$ to $C_{30}$ 2-hydroxyalkanoic acid or ester thereof together with an organic sunscreen active ingredient.

Cosmetic compositions that contain ingredients for moisturizing and/or re-hydrating and soothing the skin are plentiful. U.S. Pat. No. 4,478,853 to Chausee discloses a panthenyl moisturizer and an emollient in a non-occlusive base composition to provide enhanced conditioning and protection against dryness. U.S. Pat. No. 5,190,762 to Yarosh discloses the use of lipid encapsulated protein, such as DNA repair enzymes, to condition skin. Bertim (U.S. Pat. No. 5,106,624) discloses a cosmetic composition containing as active moisturizing agent a liposome encapsulated mineral water associated with precursors of a sulfurate glucosaminoglycans.

Accordingly, there is a need for a single cosmetic makeup product that is effective in retarding the aging effects of sunlight, retarding the natural effects of aging on the skin, such as drying and loss of elasticity and improving the appearance of damaged skin by removing dead skin, i.e. revitalizing skin, moisturizing/re-hydrating and tightening and firming skin, while also providing an attractive coloration to improve the complexion of the skin.

SUMMARY OF THE INVENTION

The present invention provides an emulsified cosmetic makeup composition for revitalizing, smoothing, moisturizing and tightening human skin comprising an aqueous carrier and emulsified and dispersed therein in cosmetically effective amounts (a) a film forming agent comprising plant polysaccharides and hydrolyzed casein;
(b) at least one sunscreen agent;
(c) at least one natural exfoliating agent;
(d) at least one moisturizer/re-hydrating agent encapsulated in liposome vessicles;
(e) at least one preservative for preventing microbial growth in the composition;
(f) at least one anti-oxidizing agent;
(g) at least one cosmetically acceptable pigment; and
(h) at least one emulsifier.

In a preferred embodiment of the invention at least one exfoliating agent (c) is an alpha hydroxy acid extract. In another preferred embodiment, the sunscreen agent (b) comprises dimethicone treated ultrafine particles of titanium dioxide coated with aluminum oxide. In yet another preferred embodiment of the invention, the at least one moisturizer/re-hydrating agent (d) comprises liposome encapsulated D-panthenol.

In another aspect of the present invention there is provided an emulsified cosmetic makeup composition for revitalizing, smoothing, moisturizing and tightening human skin comprising in an emulsified water base, based on the total weight of the composition from about 0.1 to about 12 wt % silicone-treated, aluminum oxide coated ultra fine titanium dioxide; from about 0.5 to about 24 wt % alpha hydroxyacid derived from a natural source; from about 0.1 to about 10 wt % lipid encapsulated D-panthenol; from about 0.5 to about 1.2 wt % of a film-forming agent comprising plant polysaccharides and casein hydrolyzate; from about 0.5 to about 20 wt % of at least one cosmetically acceptable pigment; from about 5 to about 10 wt % of at least one anionic emulsifier; from about 3 to about 30 wt % of at least one emollient; from about 0.5 to 1.5 wt % of at least one preservative; and from about 0.25 to about 2 wt % anti-oxidant. In a preferred embodiment, the makeup composition further comprises an amount of from about 0.7 to about 35 wt %, based on the total weight of the composition, of at least one of an anti-irritant, anti-inflammatory, healing agent or combination thereof.

In another aspect of the invention there is provided a method of revitalizing, smoothing, tightening, moisturizing and improving the complexion of the skin in humans comprising topically applying to the skin a cosmetically effective amount of an aqueous makeup composition comprising cosmetically effective amounts of a film-forming agent comprising plant polysaccharides and hydrolyzed casein; at least one sunscreen agent; at least one natural exfoliating agent; at least one moisturizer/re-hydrating agent encapsulated in liposome vessicles; and at least one cosmetically acceptable pigment.

DETAILED DESCRIPTION AND PREFERRED EMBODIMENTS

The present invention provides a cosmetic makeup composition in a pigmented emulsified base suitable for treatment of the skin. The present makeup composition contains an anti-aging component, skin revitalizing component (a natural exfolliant), moisturizer/re-hydrating component encapsulated in liposomes and a firming agent to tighten the skin and reduce the appearance of fine lines, thereby achieving multiple effects. The present emulsified cosmetic makeup composition is effective against sun-induced aging and natural aging and improves the appearance of skin already damaged by aging. When applied to the skin, the present composition retards the effects of aging caused by exposure of the skin to sunlight, moisturizes and re-hydrates dry skin, tightens the skin to provide a firming and smoothing effect, accelerates the sloughing off of dead skin to improve the complexion of the skin and provides an attractive coloration to the skin. This composition is advantageous because it combines the effects of pigmented makeups, moisturizers, re-hydrating agents, exfoliating agents, sun protection and skin tightening and firming compositions in a single composition.

The revitalizing skin cream makeup composition of the present invention contains a pigmented emulsion having dispersed therein the following essential ingredients:

(1) at least one sunscreen agent;

(2) at least one natural exfoliating agent;

(3) at least one moisturizing/re-hydrating ingredient encapsulated in liposomes;

(4) a film-forming agent comprising plant polysaccharides and hydrolyzed casein, (5) at least one cosmetically acceptable pigment;

(6) at least one cosmetically acceptable preservative;

(7) at least one anti-oxidizing agent; and (8) at least one emulsifier, each present in a cosmetically effective amount. A cosmetic makeup composition embodying the present invention is presented in Table 1. Approximate ranges of ingredients in the makeup composition are also presented in Table 1.

TABLE 1

| Ingredient | % by weight of total composition | | |
|---|---|---|---|
| | Range (Approx) | Preferred | More Preferred |
| AQUEOUS SOLVENT | 10–80 | 20–40 | 22–25 |
| SUNSCREEN AGENT | 0.1–12 | 2–10 | 6–8 |
| EXFOLIATING AGENT | 0.5–24 | 1–10 | 2–5 |
| MOISTURIZER/RE-HYDRATING AGENT | 1–15 | 0.2–11 | 0.5–5 |
| FILM FORMING SKIN TIGHTENING AGENT | 0.1–3 | 0.5–1.2 | 0.75–1 |
| PIGMENT/COLORANT | 0.5–20 | 5–18 | 7–12 |
| EMULSIFIER | 0.3–15 | 5–10 | 7–8 |
| EMOLLIENT/ANTI-IRRITANT/ ANTI-INFLAMMATORY/ HEALING AGENT | 3–30 | 10–25 | 17–20 |
| THICKENER | 0.1–3 | 0.5–1.2 | 0.75–1 |
| PRESERVATIVE | 0.05–5 | 0.5–1.5 | 0.75–1 |
| HUMECTANT | 1–8 | 5–6.5 | 5.5–6 |
| ANTI-OXIDANT | 0.01–3 | 0.25–2 | 0.5–1 |
| OPTIONAL INGREDIENTS/ ADJUVANTS | | | |
| Filler | 0.01–10 | | |
| Light Reflectant/ Smooth Feel Agent | 0.01–5 | | |
| Bodying Agent | 0.05–12 | | |

TABLE 1-continued

| | % by weight of total composition | | |
|---|---|---|---|
| | Range (Approx) | Preferred | More Preferred |
| Agent to Increase Effect of AHA/BHA | 0.50–5 | | |
| Wax | 0.10–3 | | |
| pH Buffering Agent | 0.10–1 | | |
| Fragrance | 0.05–1 | | |
| Silicone-Good Slip/Defoamer | 0.10–2 | | |

These ingredients may be dispersed in an emulsified composition by the preparation method discussed below or by any effective method of preparation. As used herein, the term "dispersal" or "dispersed" means that the ingredients are uniformly distributed in the emulsified base by any process including dissolving, emulsifying or forming a colloidal suspension, or combinations thereof. Dispersal involves sufficient mixing to eliminate powder or lumps from the composition on visual observation.

The present cosmetic makeup composition is a water based pigmented emulsion containing from about 10 to 80 wt %, preferably from about 15 to about 75 wt % water, based on the total weight of the composition. The present cosmetic makeup composition can be formulated as a foundation cream or liquid or paste makeup base, preferably as a foundation cream, e.g. under makeup cream. The cream cosmetic makeup composition of the present invention is generally an oil-in-water emulsion in which oily substances are dispersed in water with the aid of an emulsifying agent. The droplets of oil are relatively fine and uniform and protected and stabilized. The various ingredients of the revitalizing cream makeup composition of this invention are discussed below.

Anti-aging ingredients
Sunscreen Agent

The agent for retarding the aging effects of sunlight on the skin are selected from known active UV absorbing sunscreens including, for example, p-aminobenzoic acid, cinoxate, diethanolamine p-methoxycinnamate, digalloyl trioleate, dioxybenzone, ethyl 4-[bis[hydroxypropyl] aminobenzoate, 2-ethylhexyl 2-cyano-3,3-diphenylacrylate, ethylhexyl p-methoxycinnamate, 2-ethyhexyl salicylate, glyceryl aminobenzoate, homosalate (3,3,5-trimethylcyclohexylsalicylate), lawsone (2-hydroxy-1,4-naphthoquinone) with or without dihydroxyacetone, methyl anthranilate, oxybenzone, Padimate A, Padimate 0, 2-phenylbenzimidazole-5-sulfonic acid, triethanolamine salicylate, red petrolatum, and suisobenzone. Combinations of two or more sunscreen agents may also be used. In addition to the UV absorbing sunscreen agents, physical sunscreens, such as titanium dioxide, zinc oxide and the like may also be used individually or in combinations thereof.

Combinations of both UV absorbing and/or physical sunscreens may also be used in the present composition. Physical sunscreens, such as titanium dioxide or zinc oxide are preferred. Preferably, ultrafine titanium dioxide of the rutile type is used. In a most preferred embodiment, the titanium dioxide has a primary particle size of about 0.08 to 0.3 microns, as measured by laser diffraction, on a volume basis. The surface area of the primary particles of ultrafine titanium dioxide is preferably in the range of from about 35 to about 45 $m^2/g$. The UFTR grade (ultrafine) of titanium oxide, such as is commercially available from, for example, U.S. Cosmetics Corp., Dayville, Conn., is suitably used in the present invention.

Most preferably, ultrafine titanium dioxide coated with an agent, such as, for example, aluminum oxide, to provide light stability is used in the makeup composition. The coated particles may also be surface treated to reduce surface activity and, hence agglomeration. Surface treatment of titanium dioxide or titanium dioxide coated with alumina includes, for example, a silicone surface treatment, preferably a dimethicone treatment using dimethicone oil. Aluminum oxide coated, dimethicone oil treated ultrafine titanium dioxide is commercially available, such as SAT-ID-UFTR titanium dioxide, from U.S. Cosmetics Corp., Dayville, Conn.

When zinc oxide is used as the sunscreen component of the present cosmetic composition, it is preferred that it be used together with another sunscreen, such as one of the UV absorbing type sunscreens such as listed above, since zinc oxide is recognized by the FDA as a category III sunscreen.

The sunscreen component of the present invention is preferably used at an effective amount to provide a sun protection factor (SPF) of about 10, although the amount of sunscreen component can be varied to provide the desired SPF, generally in the range of from about 4 to about 30. Although the amount of the sunscreen component of the present cosmetic composition will depend, in general, on the type and/or absorption properties, it will generally be in the range of from about 0.1 to about 12 wt % of the total composition, preferably in the range of from about 2 to 10 wt % and most preferably from about 6 to 8 wt % based on the total weight of the composition.

The sunscreen agent of the present cosmetic makeup composition may also include an agent to boost sunscreen efficacy by scattering light, such as for, example ELEFAC™ I-205, a dry isoarachidyl neopentanoate emollient available from Bernel Chemical, Co., Englewood, N.J.

Exfoliating Agent

The cosmetic makeup composition of the present invention contains a natural (non-synthetic) exfoliating agent (revitalizing agent) to accelerate the natural sloughing off of dead skin, which provides a more youthful complexion and appearance. The exfoliating agent is preferably one which is water-soluble, such as the alpha hydroxyacids (AHA), and may be derived from natural fruit sources, licorice root or molasses, for example. These sources contain a high amount of lactic acid and may also contain one or more of the following other carboxylic acids, such as glycolic acid, citric acid, malic acid, decanoic acid, octanoic acid, tartaric acid or pyruvic acid, for example. The exfoliating agent may also be selected from beta hydroxyacids (BHA), preferably derived from natural sources, such as salicylic acid, for example. However, alpha hydroxyacids acids are preferred since, being water-soluble, alcohol is not required for solubilizing the alpha hydroxyacids. Thus, with cosmetic compositions containing alpha hydroxyacids drying of the skin is minimized.

The alpha or beta hydroxyacids may be present as free acids, or in the form of derivatives, such as peroxides, lactones, amides, esters or salts formed by reacting the compound with, for example, ammonium hydroxide, or organic or inorganic bases.

Preferably, alpha hydroxyacid derived from molasses that is high in lactic acid or a licorice extract that is high in lactic acid is used. BIOLAC™, a commercially available product from Barnet Products Corp., Englewood Cliffs, N.J. has been effectively used as the exfoliating agent in compositions according to the invention. This alpha hydroxyacid is a high purity natural lactic acid extract obtained from molasses and contains only trace amounts of pyruvic acid and other non-alpha biological materials.

The natural exfoliating agent may be used in an amount in the range of from about 0.5 to about 24 wt % preferably, about 1 to 10 wt %, based on the total weight of the cosmetic composition.

Moisturizers/Re-hydrating Ingredients

The cosmetic makeup composition of the present invention contains at least one liposome-encapsulated or phospholipid-encapsulated moisturizer or re-hydrating agent and, preferably, an encapsulated blend of moisturizing/re-hydrating ingredients. For example, the encapsulated moisturizer or re-hydrating agent may be D,L-panthenol, D-panthenol, vitamin A palmitate, vitamin E acetate, methylsilanetriol mannuronate, natural oils such as tallow oil, macadamia nut oil, borage oil, evening primrose oil, kukui nut oil, rice bran oil, tea tree oil, a medium chain fatty acid ester of glycerol, such as glycerol triheptanoate, glyceryl trioctanoate, glycerol trioctanoate, mineral water, silicones, silicone derivatives. Mixtures of two or more of these ingredients may be used. A preferred moisturizer is D-panthenol, such as a liposome vessicle containing D-panthenol. This product is commercially available, such as BROOKOSOME™ DP, which is a cosmetic phospholipid vessicle encapsulating D-panthenol. Other moisturizers/re-hydrating agents may also be incorporated in the form of phospholipid encapsulated vessicles, Such as, for example, phospholipid encapsulated Vitamin E and phospholipid encapsulated mineral water.

Preferably, the total amount of moisturizer/re-hydrating component of the present makeup composition is in the range of from about 0.1 to about 15 wt % based on the total weight of the composition, and most preferably in the range of from about 0.2–11 wt % of the total composition. The amount of liposome encapsulated moisturizer/re-hydrating agent is generally in the range of from 0.10 to 10.0 wt % of the total composition.

Film Forming Skin Tightening Agent

The makeup composition of the present invention also contains as an essential ingredient, a film forming skin tightening agent, particularly a plant derived biological polysaccharide cosmetic ingredient which may be combined with a casein hydrolyzate. The polysaccharides which can be used in the practice of the invention include, for example, lecithin, pectin, karaya gum, locust bean gum, xanthan gum and mixtures thereof. The polysaccharides are preferably used in the present compositions in combination with a casein hydrolyzate. An especially preferred film forming skin tightening agent of the present invention is Pentacare™ HP, a commercially available blend of plant polysaccharides and hydrolyzed casein from Pentapharm LTD., Basel, Switzerland.

The polysaccharides and hydrolyzed casein forms a film on the skin, helping to tighten the skin and smooth wrinkles and fine lines. It also results in an optically smoothing effect.

Generally, the film forming agent is used in an amount of from about 0.1 to 3% based on the total weight of the composition and preferably in an amount of about 0.5% to about 1.2% based on total weight of the composition.

Colorant

The present cosmetic makeup composition also contains at least one of various cosmetically acceptable inorganic pigments or colorants, such as, for example titanium dioxide, yellow pure oxy, black pure oxy, pink lomicron, russet iron oxide, titanium dioxide, talc, red iron oxide, D & C Red #30 Lake, FD&C Yellow #6 Aluminum Lake and combinations thereof. The combination of pigments and amount of pigment or colorant incorporated into the present composition depends upon the particular color desired, however, in general an amount of pigment or colorant in the range of from about 0.5 to 20 wt %, preferably, 5 to 18% is used.

Preservative

The cosmetic makeup composition is manufactured under clean but non-sterile conditions, therefore preservatives are used to prevent growth of microorganisms. A sufficient quantity of one or more preservatives is added to the makeup composition so that the emulsified cosmetic makeup composition withstands bacterial growth from an experimental inoculation for at least three months.

The cosmetic makeup composition can be prepared with, for example, natural antimicrobial agents, such as tea tree oil and cedar oil, or organic preservatives such as, propylene glycol, trisodium EDTA, methylparaben, propylparaben, ethylParaben butylparaben, phenoxy ethanol, hexamidine isotionate, commercially prepared products such as GERMALL™ II and GLYDANT™, for example, and combinations thereof. The amount of preservative incorporated into the present composition is generally in the range of from about 0.05 to about 5.0 wt %, preferably, from about 0.5 to 1.5 wt % based on the total weight of the composition. Propylene glycol can be added in amounts sufficient so as to serve as a humectant and preservative of the cosmetic composition, such as from about 1.0 to 8.0 wt %, preferably from about 5.0 to 6.5 wt % based on the total weight of the composition.

Antioxidants

To maintain the color of the present makeup composition and prevent malodorous developments, any of the known antioxidants may be included in the cosmetic composition. Examples of suitable antioxidants include TENOX II, obtained from Eastman Chemical Products, Inc., Kingsport, Tenn. and vitamin E USP, a natural antioxidant. However, other known antioxidants, alone or in combination, can be included in the present cosmetic makeup composition, such as, for example, Vitamin C esters, magnesium ascorbyl phosphate, ascorbyl dipalmitate, licorice extracts, mulberry extract and green tea extract. The anti-oxidant is incorporated in an amount of from about 0.01 to about 3 wt %, preferably from about 0.25 to 2 wt % based on the total weight of the composition.

Emollients, Anti-Irritating, Anti-Inflammatory, and/or Healing Agents

The present cosmetic makeup composition preferably also contains an amount of at least one emollient to provide a soothing and softening effect to the skin and can include at least one anti-irritant agent, anti-inflammatory agent, healing agent or combination thereof. These ingredients may be added to the cosmetic makeup composition in an amount of from about 3 to about 30 wt %, preferably about 10 to about 20 wt % of the total weight of the composition to offset the possible irritating effects of the acid, i.e. alpha- or beta hydroxyacid, used as the exfoliating agent. Examples of calming, soothing and softening agents which may be included in the present cosmetic makeup composition include Vitamin A palmitate; Phytelene Complex EGX 244, which is a botanical blend of extracts of calendula, chamomile, linden, cornflower, matricaria and hypericum; allantoin; dipotassium glycyrrhizinate; stearyl glycyrrhizinate; bisabolo((3-cyclohexene-1-methanol-$\alpha$,4-dimethyl-$\alpha$ (4-methyl-3-pentenyl)); squalane NF; squalane EX; cetyl ester wax; orange roughy oil; hydrogenated phospholipids, and HETESTER™ FAO, which is a $C_{12}$–$C_{15}$ alcohol octanoate, available from Bernel Chemical Company, Englewood, N.J. Suitable emollients can be employed if desired. Those emollients include the following classes, for example:

1. hydrocarbon oils and waxes, such as mineral oil, polyethylene and paraffin;
2. triglyceride esters, such as olive oil, avocado oil, and squalene;
3. lanolin and derivatives;
4. ether-esters, such as fatty acid esters of ethoxylated fatty alcohols; and
5. fatty acids having 10 to 20 carbon atoms, such as lauric, myristic, oleyl, and stearate. A particularly preferred anti-irritant that may be incorporated into the present cosmetic composition is dipotassium glycyrrhizic acid. Glycyrrhizic acid is a glycyrrhetinic acid glycoside obtained from natural licorice plant extracts.

Thickener

Preferably the cosmetic makeup composition contains sufficient thickener that it does not run off the face and other skin areas when applied. The thickeners complement the function of emulsifiers in holding together the water and oil phases of the composition. A preferred thickener of the present cosmetic makeup composition includes xanthan gum. Other thickeners which may be used in place of or together with xanthan gum include, for example, sodium polyacrylate, starch and the like. The thickener generally comprises from about 0.01 to about 3 wt % of the composition, preferably about 0.5 to about 1.2 wt % of the composition.

Emulsifier

At least one emulsifier is combined with water, preferably demineralized water, to form the emulsified base of the present cosmetic makeup composition. The emulsifier forms a stable bridge between the water and any oil of the other ingredients of the composition. Preferably, an anionic emulsifier, such as AmphiSol™, which is a DEA cetyl phosphate anionic oil-in-water emulsifier functional even at low pH, i.e., between pH 3.5 to 6.0, and is available commercially from Bernel Chemical Co., Englewood, N.J. may be used in the present cosmetic makeup composition, either alone or in combination with other emulsifiers, preferably other anionic emulsifiers. The use of anionic emulsifiers in the present cosmetic makeup composition is desirable since nonionic emulsifiers can interfere with preservatives included in the composition and cationic emulsifiers are difficult to stabilize and usually do not provide a cosmetically elegant product.

The amount of emulsifier incorporated in the present composition is in the range of about 0.3 to about 15 wt %, preferably, about 5 to about 10 wt %.

Other suitable emulsifiers, preferably anionic emulsifiers, may be used and include, for example, fatty acid soaps, e.g. sodium, potassium and triethanolamine soaps, wherein the fatty acid moiety contains from 10 to 20 carbon atoms; alkali metal, ammonium or substituted ammonium alkyl sulfates; alkyl arylsufonates; and alkyl ethoxy ester sulfonates having 10 to 30 carbon atoms in the alkyl moiety and 1 to 50 ethylene oxide units. Typical of the useful commercially available emulsifiers, mention can be made of Amphisol™, Lipo GMS 450, Solulan C-24, glucamate SSE 20 and glucate SS.

Other Optional Adjuvants

Various other cosmetically acceptable ingredients can be included in the cosmetic makeup composition of the present invention, including, for example, fragrance, defoamers, such as a silicone or silicone derivative material, pH buffers, such as triethanolamine, bodying agents, such as stearic acid and cetyl alcohol, light reflectants, fillers, such as talc, wax to provide a cushioning effect, polymer based deposition and delivery compounds such as Polyolprepolymer 2, and humectants, such as hyaluronic acid. These optional ingredients can be added alone or in combination and where used are added in cosmetically effective amounts. Approximate ranges of amount of and examples of each of these optional ingredients are listed in Table 1.

Preferably, light reflectant particles, such as Micronosphere M, available from Rona, Inc., Hawthorne, N.Y. are added to the present cosmetic makeup composition. Micronosphere™ M is a blend of fine mica particles having a size of less than about 15 $\mu$m coated with submicron (less than about 15 $\mu$m) silica spheres. The silica spheres are uniform in shape and size and act as ball bearings causing the mica particles to slide across each other upon application to the skin. The result is exceptionally good feel. Moreover, the spheres prevent excessive oil absorption and serve as an SPF enhancer. The Micronosphere™ M ingredient also functions to scatter light giving a soft focus look that minimizes the appearance of fine lines.

In a preferred embodiment, the cosmetic makeup composition of this invention contains from 0.1 to 5.0 wt % of a polyalkylene glycol based polymer such as Polyolprepolymer 2 available from Barnet Products, Corp., Englewood, N.J. Polyolprepolymer 2 is a highly lipophilic oligomer having an average molecular weight of about 4,000, which forms a non-invasive film that remains on the upper layers of the skin where it acts as a delivery and/or deposition system for other cosmetic ingredients, such as alpha hydroxyacids. The lipophilic oligomer penetrates the stratum corneum but does not penetrate the skin further. It acts as a reservoir within the upper layers of the skin, subsequently slowly releasing any ingredient(s) that have previously been dissolved in it, thus resulting in increased efficacy and reduction of irritation.

In a most preferred embodiment, the lipophilic oligomer can have another active component of the composition, such as, alpha hydroxyacid dissolved in the lipophilic oligomer prior to its addition to the composition. The Polyolprepolymer 2 component serves as a reservoir to slowly release the alpha hydroxyacid, thereby reducing any irritation which may be caused by the acid on sensitive skin.

The present cosmetic makeup composition can also contain an amount of from about 0.5 to about 15 wt %, preferably about 1 to about 10% of humectant ,such as propylene glycol, hyaluronic acid, sphingolipid CB-1, phytoglycolipid, PCA derivatives, or combinations thereof.

Preparation of Cosmetic Makeup Composition

The cosmetic makeup composition of the invention can be formulated as a foundation cream or liquid or paste makeup base, whereby beneficial effects are produced by application of the makeup composition to the skin.

The cosmetic makeup composition of the invention can be prepared by a batch operation or by in-line blending techniques. Referring to Table 2, the makeup composition is prepared by forming a first mixture by combining the ingredients of mixture A (Table 2) at room temperature and then heating the ingredients to 75° to 80° C. until a uniform dispersion is obtained, at which time the separately formed mixture B (Table 2) is added and mixed until smooth, while maintaining the temperature. The components of mixture C (Table 2) are then added and mixed until a uniform blend is obtained. The color mix (mixture D) (Table 2) is formed in a two-step process described below and then added with mixing and the batch is tested for color quality. Emulsifier is added and mixed until a uniform water/pigment phase is obtained. This mixture is heated to 77° to 80° C.

Mixture F is formed separately by mixing the ingredients (Table 2) at room temperature and heating to 77° to 80° C. until a smooth oil phase is obtained, after which mixture F is added to the water/pigment phase at a rate that allows incorporation of the oils without excessive flotation on the surface. The mixture is maintained at 77° to 80° C. under agitation. Premixed mixture G (Table 2) is added to the batch for pH buffering and the batch is cooled to 45° to 50° C., while mixing.

Mixture H (Table 2) is premixed and added to the batch and further mixed. The alpha/beta hydroxyacids are added, mixed and the ingredients of mixture J (Table 2) are added one at a time (the order does not effect the results) and the mixture is cooled to 30° to 35° C. The batch is further mixed and strained.

Mixture D is obtained by milling the colorants to disperse the various pigments uniformly and then mixing the uniformly dispersed colorants with the sunscreen and spherical particles until a uniform dispersion is obtained.

TABLE 2

Method of Preparation of Cosmetic Makeup Composition

| Ingredient | Concentration % by weight of total composition |
|---|---|
| BLEND | |
| Mixture A | |
| Demineralized water | 22.90 |
| Veegum Ultra (thickener) | 1.00 |
| Methyl paraben (preservative) | 0.30 |
| Glucamate SSE-20 (emulsifier) | 2.00 |
| Allantoin (skin protectant) | 0.2 |
| Dipotassium Glycerrizinate (anti-irritant) | 0.1 |
| Mixture B | |
| Propylene Glycol (humectant) | 6.00 |
| Keltrol F (thickener) | 0.20 |
| Mixture C | |
| 200 Fluid 100 cst (silicone) | 0.50 |
| Amphisol ™ M (emulsifier) | 0.10 |
| Mixture D | |
| Part 1 | |
| Titanium Dioxide 7300 | 31.25 |
| Altalc 400 | 27.613 |
| Yellow Iron Oxide 7055 | 5.129 |
| Russet Iron Oxide (Colorants) | 0.392 |
| Lomicron Pink 2511 | 1.771 |
| Pure Oxy Black BC 3190 | 0.512 |
| Part 2 | |
| SAT-ID-UFTR (sunscreen) | 29.17 |
| Microsphere ™ M (light reflectant) | 4.17 |
| Mixture E | |
| Amphisol ™ M (emulsifier) | 0.9 |
| Mixture F | |
| Wickenol 151 | 6.5 |
| Hetester FAO (emollients) | 5.5 |
| Syncelane 30 | 5.0 |
| Stearic acid (bodying agent) | 1.5 |
| Glucate SS (emulsifier) | 1.5 |
| Lipo GMS (emulsifier) | 1.75 |
| Polyolprepolymer 2 (polyalkylene glycol polymer deposition/delivery system) | 2.0 |
| Tenox BHT (anti-oxidant) | 0.05 |
| Cetyl Alcohol (bodying agent) | 2.0 |
| Vitamin A Palmitate (moisturizer) | 0.1 |
| Pelemol ISB (emollient) | 2.0 |
| Vitamin E Acetate (anti-oxidant) | 0.1 |
| Elefac I-205 (emollient; SPF booster) | 2.0 |
| Propylparaben (preservative) | 0.2 |

TABLE 2-continued

Method of Preparation of Cosmetic Makeup Composition

| Ingredient | Concentration % by weight of total composition |
|---|---|
| Super Hartolan (wax) | 0.75 |
| Mixture G | |
| Triethanolamine 99% (pH buffer) | 0.7 |
| Deionized Water | 1.0 |
| Mixture H | |
| Deionized Water | 1.0 |
| Germall II (preservative) | 0.25 |
| Glydant (preservative) | 0.2 |
| Mixture I | |
| Biolac ™ (AHA-molassis extract) | 2.0 |
| Mixture J | |
| Brookosome ™ DP (liposome moisturizer) | 2.5 |
| Pentacare ™ HP (skin tightening agent) | 1.0 |
| Phytelene Complex EGX 244 (botanical anti-inflammatory skin softener) | 1.0 |
| Fragrance AN 101651 | 0.2 |

EXAMPLE 1

Preparation of a Cream Makeup Composition

A. Formulation

| PART 1 | |
|---|---|
| 24.9% | Water |
| 1.0% | Veegum ultra (thickener) |
| 2.0% | BIOLAC ™ (AHA) |
| 0.2% | Allantoin (skin protectant) |
| 0.1% | Dipotassium glycerrhizinate (anti-irritant) |
| 6.0% | Propylene glycol (humectant) |
| 0.2% | Keltrol F (thickener) |
| 0.5% | 200 Fluid 100 cst (silicone, defoamer) |
| 1.0% | Amphisol ™ (emulsifier) |
| 1.5% | Glucate SS (emulsifier) |
| 24.0% | Pigment/sunscreen MIXTURE D |
| 2.0% | Pelemol (emollient) |
| 6.5% | Wickenol ™ (emollient) |
| 5.5% | Hetester FAO (emollient) |
| 5.0% | SYNCELANE 30 (emollient) |
| 2.0% | Cetyl Alcohol (bodying agent) |
| 1.5% | Stearic acid (bodying agent) |
| 2.0% | Glucamate (emulsifier) |
| 1.0% | Solucan (emulsifier) |
| 1.75% | LIPO GMS 450 (emulsifier) |
| 2.0% | Polyolprepolymer 2 (delivery/deposition compound) |
| 0.05% | Tenox BHT (anti-oxidant) |
| 0.1% | Vitamin E acetate (anti-oxidant) |
| 0.1% | Vitamin A Palmitate (moisturizer) |
| 2.0% | ELEFAC ™ I-205 (emollient SPF booster) |
| 1.0% | Pentacare ™ HP (film forming agent) |
| 1.0% | Phytelene Complex ™ EGX 244 (skin softener and anti-inflammatory) |
| 0.75% | Super Hartolan (Wax) |
| 0.2% | Fragrance AN 101651 |
| 0.2% | Propylparaben (preservative) |
| 0.25% | GERMAC (preservative) |
| 0.2% | GLYDANT (preservative) |
| 0.3% | Methylparaben (preservative) |

| PART 2 | |
|---|---|
| 31.25% | Titanium Dioxide 7300 (pigment) |
| 27.613% | ALTALC 400 (pigment) |
| 5.129% | Yellow Iron Oxide 7055 (Pigment) |
| 0.392% | Russet Iron Oxide C33-5138 (pigment) |
| 1.771% | Lomicron Pink 2511 (pigment) |
| 0.512 | Pure Oxy Black BG3190 (pigment) |
| 29.17% | SAT-ID-UFTR (sunscreen) |
| 4.17% | MICRONOSPHERE ™ M (light reflectant, good feel agent) |

B. Preparation

The cosmetic cream makeup of formulation A is made as follows: nine separate mixtures, listed below are prepared and blended.

Mixture A is prepared by adding 1.0 kg Veegum Ultra to 22.9 kg water at room temperature under moderate agitation. When mixing is complete the temperature is increased to 75° to 80° C. and 0.3 kg methyl praben, 0.2 kg allantoin, 0.1 kg dipotassium glycyrrhizinate and 2.0 kg glucamate SSE-20 are added and mixed.

Mixture B is formed in a separate vessel. 6 kg propylene glycol and 0.2 kg Keltrol F are mixed until uniform and then added to Mixture A and blended at 75° to 80° C.

Mixture C consists of 0.5 kg 200 fluid 100 CS and 0.1 kg Amphisol. These ingredients are mixed into the above blend and mixed at 75° to 80° C. until a completely uniform mixture is obtained.

Mixture D is the composition of Part 2 above. This mixture is obtained by mixing and milling all of the listed pigments in a CBM Powder Mixer until well blended, approximately 15 to 25 minutes. The SAT-ID-UFTR (19.186 kg) and Micronosphere™ M (4.17 kg) are then added and milling is continued.

24 kg of Mixture D is blended into the composition of Mixture C and mixed until uniform.

Mixture E consists of 0.9 kg Amphisol™, which is added to the pigmented composition at 75° to 80° C.

The ingredients of Mixture F are mixed separately at 75° to 80° C. and slowly added to the pigmented composition at a rate that allows ready incorporation of the oils without excessive flotation at the surface. Mixture F contains 6.5 kg Wickenol 151, 5.5 Kg Hetester FAO, 5.0 kg Syncelane 30, 1.5 kg Stearic acid, 1.5 kg GLUCATE, SS 1.75° kg Lipo GMS, 2.0 kg Polyolprepolymer 2, 1.0 kg SOLULAN C-24, 0.05 TENOX BHT™, 2.0 kg cetyl alcohol 0.1 kg Vitamin A palmitate, 2.0 kg PELEMOL™ ISB, 0.1 Kg Vitamin E acetate, 2.0 kg ELEFAC™ I205, 0.2 kg propylparaben and 0.75 kg Super Hartolan.

The mixture is then heated to 77° to 80° C. to form an oil phase.

The ingredients of Mixture G ( 8.7 kg triethanolamine 99% and 1.0 kg water) are premixed and added to the oil phase. The composition is then force cooled to 45–50° C.

The ingredients of Mixture H (1.0 kg water, 0.25 KG GERMAL™ II and 0.2 kg Glydant) are premixed and added to the cooled composition and mixed until the composition is clear.

2.0 kg BIOLAC™ (Mixture I) is added to the clear composition and mixed.

The following ingredients are added to the composition one at a time (2.50 kg BROOKOSOME™ DP, 1.0 kg PENTACARE™ HP, 1.0 kg PHYTELENE™ Complex EGX 244 and 0.2 kg fragance AN10165 and mixed while cooling the composition to 30°–35° C.

Although the present invention has been described with reference to a preferred embodiment thereof, other versions of the cosmetic makeup composition are possible. Therefore, the spirit and scope of the appended claims should not be limited to the preferred version contained herein.

The cosmetic makeup composition of the present invention is topically applied in a conventional manner, as by dispersing from a container as needed. The composition is easily spread on the skin surface and leaves the skin with a soft and smooth appearance. The makeup composition of the present invention is formulated to exert the following desirable effects: (1) anti-stress, calming, and soothing effects, (2) anti-aging effects, (3) revitalizing effects, (4) moisturizing and hydrating effects, (5) firming and elasticity effects and (6) anti-wrinkle effects.

What is claimed is:

1. An emulsified cosmetic makeup composition for revitalizing, smoothing, moisturizing and tightening human skin comprising in an emulsified water base, based on the total weight of the composition, from about 0.1 to about 12 wt % silicone surface treated, aluminum oxide coated titanium dioxide having a particle size in the range of from about 0.08 to 0.3 micron; from about 0.5 to about 24 wt % alpha hydroxyacid; from about 0.1 to about 10 wt % lipid encapsulated D-panthenol; from about 0.5 to about 1.2 wt % of a film-forming agent comprising plant polysaccharides and casein hydrolyzate; from about 0.5 to about 20 wt % of at least one cosmetically acceptable pigment; from about 0.3 to about 10 wt % of at least one anionic emulsifier; from about 3 to about 30 wt % of at least one emollient; from about 0.5 to 1.5 wt % of at least one preservative; and from about 0.25 to about 2 wt % antioxidant.

2. The cosmetic makeup composition as set forth in claim 1 further comprising an amount of from about 0.7 to about 35 wt %, based on the total weight of the composition of at least one of an anti-irritant agent, anti-inflammatory agent, healing agent or combination thereof.

3. The cosmetic makeup composition as set forth in claim 1 further comprising an amount of from about 0.01 to about 3 wt %, based on the total weight of the composition, of light reflectant particles.

4. The cosmetic makeup composition as set forth in claim 1 further comprising an amount of from about 0.5 to 5 wt %, based on the total weight of the composition of a polyalkylene glycol polymer deposition and delivery agent.

5. An emulsified cosmetic makeup composition for:revitalizing, smoothing, moisturizing and tightening human skin comprising an aqueous carrier constituting from about 15 to 75% by weight of the composition, and having emusified and dispersed therein (a) from about 0.5 to 1.2% by weight of film forming agent comprising plant polysaccharide and hydrolyzed casein;
(b) from about 2 to 10% by weight of sunscreen agent;
(c) from about 1 to 10% by weight of alphahydroxy acid exfoliating agent;
(d) from about 0.2 to 11% by weight of liposome vesicle encapsulated moisturizer/rehydrating agent;
(e) from about 0.5 to 1.5% by weight of preservative for preventing microbial growth in the composition;
(f) from about 0.25 to 2% by weight of antioxidant;
(g) from about 5 to 18% by weight of cosmetically acceptable pigment;
(h) from about 0.3 to 10% by weight of anionic emulsifier;
(i) from about 0.01 to 5% by weight of light reflectant particles;
(j) from about 0.05 to 12 by weight of bodying agent;
(k) from about 0.10 to 3% by weight of wax;
(l) from about 0.10 to 1% by weight of pH buffering agent;

(m) from about 0.05 to 1% by weight of fragrance; and
(n) from about 0.10 to 2% by weight of antifoam agent.

6. An emulsified cosmetic makeup composition which comprises, on a weight basis,

| | |
|---|---|
| water, | about 25% |
| thickener, | about 1.2% |
| alpha hydroxy acid, | about 2% |
| skin protectant, | about 0.2% |
| anti-irritant, | about 0.1% |
| humectant, | about 6% |
| silicone defoamer, | about 0.5% |
| emulsifier, | about 7% |
| pigment and sunscreen, | about 24% |
| emollient, | about 21% |
| bodying agent, | about 3.5% |
| polyolprepolymer delivery/deposition agent, | about 2% |
| anti-oxidant | about 0.15% |
| moisturizer, | about 0.1% |
| polysaccharide-hydrolyzed casein film-forming agent, | about 1.5% |
| plant extract skin-softener and anti-inflammatory agent, | about 1% |
| wax, | about 0.75% |
| liposome encapsulated D-panthenol, | about 2.5% |
| fragrance, | about 0.2%, and |
| preservatives, | about 1%. |

7. An emulsified cosmetic makeup composition for revitalizing, smoothing, moisturizing and tightening human skin, comprising an aqueous carrier and emulsified and dispersed therein, on a weight basis, (a) about 0.5 to 1.2% of a blend of plant polysaccharide and hydrolyzed casein, effective as a film-forming skin tightening agent;
(b) about 5 to 18% of aluminum oxide coated, dimethicone oil surface treated rutile type titanium dioxide effective as a sunscreen agent;
(c) about 1 to 10% of exfoliating agent comprising a lactic acid containing extract of molasses;
(d) about 0.5 to 5% of liposome- or phospholipid-encapsulated D-panthenol, effective for moisturizing and rehydrating skin;
(e) an antimicrobial effective amount of preservative;
(f) antioxidant in an amount effective for inhibiting discoloration of the composition;
(g) a coloring effective amount of cosmetically acceptable colorants; and
(h) an emulsifying effective amount of anionic emulsifier.

8. An emulsified cosmetic makeup composition for revitalizing, smoothing, moisturizing and tightening human skin, comprising an aqueous carrier and emulsified and dispersed therein, on a weight basis, (a) about 0.5 to 1.2% of a blend of plant polysaccharide and hydrolyzed casein, effective as a film-forming skin tightening agent;
(b) about 5 to 18% of aluminum oxide coated, dimethicone oil surface treated rutile type titanium dioxide effective as a sunscreen agent;
(c) about 1 to 10% of exfoliating agent comprising a lactic acid containing extract of molasses;
(d) about 0.5 to 5% of liposome- or phospholipid-encapsulated D-panthenol, effective for moisturizing and rehydrating skin;

(e) an antimicrobial effective amount of preservative;

(f) antioxidant in an amount effective for inhibiting discoloration of the composition;

(g) a coloring effective amount of cosmetically acceptable colorants;

(h) an emulsifying effective amount of anionic emulsifier;

(i) a skin softening effective amount of a botanical blend of extracts of calendula, chamomile, linden, cornflower, matricaria and hypericum;

(j) an anti-irritating effective amount of dipotassium glycyrrhizic acid;

(k) a skin protecting effective amount of allantoin; and (l) a soothing and softening effective amount of cosmetically acceptable emollients.

9. The composition of claim 8 further comprising (m) a light scattering effective amount of light reflectant particles.

10. A method of revitalizing, smoothing, tightening, and moisturizing and improving the complexion of the skin in humans comprising topically applying to the skin a cosmetically effective amount of an aqueous makeup emulsified composition comprising cosmetically effective amounts of a film-forming agent comprising plant polysaccharides and hydrolyzed casein; at least one sunscreen agent comprising silicone surface treated aluminum oxide coated titanium oxide particles having a particle size in the range of from about 0.08 to 0.3 microns; at least one exfoliating agent selected from the group consisting of alpha hydroxy acids and beta hydroxy acids; at least one moisturizer/re-hydrating agent comprising D-panthenol encapsulated in liposome vesicles; a botanical blend of extracts of calendula, chamomile, linden, cornflower, matricaria and hypericum; allantoin; dipotassium glycyrrhizinate; stearyl glycyrrhizinate; and at least one cosmetically acceptable pigment and an emulsifying effective amount of an anionic emulsifier.

* * * * *